United States Patent [19]

Yagasaki et al.

[11] Patent Number: 5,376,545
[45] Date of Patent: Dec. 27, 1994

[54] DNA CODING FOR URICASE AND PROCESS FOR PRODUCING URICASE

[75] Inventors: Makoto Yagasaki; Shuichi Ishino; Kazuhisa Iwata; Masaki Azuma, all of Hofu; Sadao Teshiba; Masaru Hasegawa, both of Machida; Kazuo Yamaguchi, Sagamihara; Keiichi Yano, Machida; Yoshiharu Yokoo, Ushiku; Yukio Hashimoto, Yamato, all of Japan

[73] Assignee: Kyowa Hakko Kogyo Co., Ltd., Tokyo, Japan

[21] Appl. No.: 985,690

[22] Filed: Dec. 3, 1992

[30] Foreign Application Priority Data

Dec. 4, 1991 [JP] Japan .................. 3-320525

[51] Int. Cl.$^5$ ............ C12N 9/06; C12N 15/53; C12N 15/70
[52] U.S. Cl. .................. 435/191; 435/320.1; 435/252.33; 536/23.2
[58] Field of Search ............ 435/191, 320.1, 252.33; 536/23.2

[56] References Cited

U.S. PATENT DOCUMENTS

| 4,882,280 | 11/1989 | Takashio et al. ............ 435/228 |
| 4,987,097 | 11/1991 | Takashio et al. ............ 435/171 |

FOREIGN PATENT DOCUMENTS

| 42-5192 | 1/1967 | Japan . |
| 44-14783 | 7/1969 | Japan . |
| 60-19990 | 5/1985 | Japan . |
| 61-280272 | 12/1986 | Japan . |
| 253488 | 2/1990 | Japan . |
| 2221910 | 2/1990 | United Kingdom . |

OTHER PUBLICATIONS

Machida, Y., et al. (1980) Agric. Biol. Chem 44(12), 2811–2815.
Watanabe, Y., et al. (1969) Agric. Biol. Chem. 33(9), 1282–1290.

*Primary Examiner*—Charles L. Patterson, Jr.
*Attorney, Agent, or Firm*—Antonelli, Terry, Stout & Kraus

[57] ABSTRACT

The present invention provides a DNA coding for uricase from the genus Cellulomonas and a process for producing uricase using a microorganism which carries a recombinant DNA containing the DNA.

10 Claims, 5 Drawing Sheets

DNA CODING FOR URICASE AND PROCESS FOR PRODUCING URICASE

BACKGROUND OF THE INVENTION

The present invention relates to DNA coding for uricase and a process for producing uricase. More specifically, the present invention relates to DNA coding for uricase, isolated from a microorganism belonging to the genus Cellulomonas, a recombinant plasmid containing said DNA, a transformant which carries said recombinant plasmid, and a process for producing uricase by culturing said transformant. The present invention further relates to a process for producing uricase by culturing a non-genetically engineered microorganism belonging to the genus Cellulomonas and being capable of producing uricase.

Uricase (EC 1.7.3.3) is an enzyme which catalyzes a reaction which oxidizes uric acid to produce allantoin, hydrogen peroxide and carbon dioxide, and is used for determining uric acid in the blood or urine, and usable as a component in a hair-dyeing kit, etc.

Heretofore, uricase has been produced by various microorganisms of the genera Candida (Japanese Published Examined Patent Application No. 5192/67), Micrococcus, Brevibacterium (Japanese Published Examined Patent Application No. 14783/69), Streptomyces (Agric. Biol. Chem. 33, 1282, 1969), Enterobacter (Japanese Published Examined Patent Application No. 19990/85; Agric. Biol. Chem., 44, 2811, 1980), and Bacillus (Japanese Published Unexamined Patent Application No. 280272/86, U.S. Pat. Nos. 4,882,280 and 4,987,076; Japanese Published Unexamined Patent Application No. 53488/90, GB 2221910A).

However, the known processes are still insufficient in efficiency of the production of uricase. There is a great demand for a process for producing uricase, in higher yield and at lower cost.

As the result of extensive studies in the process for producing uricase, it has now been found that a large amount of uricase can be produced by isolating DNA which codes for uricase from a microorganism belonging to the genus Cellulomonas, constructing a recombinant plasmid containing said DNA, transforming a suitable host strain with said recombinant plasmid, and culturing said transformant.

SUMMARY OF THE INVENTION

In accordance with a first aspect of the present invention, there is provided an isolated DNA which codes for uricase having the amino acid sequence as defined in the Sequence Listing by SEQ ID NO: 1. Also included in the first aspect are: a recombinant plasmid containing that DNA, a transformant carrying that plasmid, and the use of that transformant to produce uricase in a culture medium prior to the recovery of that uricase from the culture medium.

In another aspect of the present invention, there is provided a modified DNA coding for uricase, that modified DNA having the nucleotide sequence as defined in the Sequence Listing by SEQ ID NO: 13.

In yet another aspect of the present invention, there is provided a process for producing uricase which comprises culturing, in a culture medium, a microorganism belonging to the genus Cellulomonas and capable of producing uricase in the culture, and recovering the product uricase from the culture.

DETAILED DESCRIPTION OF THE INVENTION

Any microorganism belonging to the genus Cellulomonas capable of producing uricase can potentially serve as the nucleic acid source for the molecular cloning of the gene coding for uricase. A preferred example is the strain Cellulomonas flavigena SK-4, which has been deposited with the Fermentation Research Institute, the Agency of Industrial Science and Technology of Japan as FERM BP-1575 as of Nov. 21, 1987 under the conditions of the Budapest Treaty. The general bacteriological characteristics of the microorganisms belonging to the species Cellulomonas flavigena are described in Bergey's Manual of Systematic Bacteriology, Vol. 2, pp. 1325–1329 (1986).

Uricase-producing microorganism of the genus Cellulomonas may be cultured aerobically in a culture medium containing a carbon source, a nitrogen source and the inorganic salts and other growth factors necessary to the growth of the microorganism.

As the carbon source, various carbohydrates such as glucose, fructose, sucrose, molasses, blackstrap molasses and starch hydrolyzates; alcohols such as ethanol, glycerin and sorbitol; organic acids such as pyruvic acid, lactic acid and acetic acid; and amino acids such as glycine, alanine, glutamic acid and aspartic acid, may be used as long as the carbon source can be assimilated by the microorganism.

As the nitrogen source, ammonia, various inorganic or organic ammonium salts such as ammonium chloride, ammonium sulfate, ammonium nitrate, ammonium carbonate, ammonium acetate and ammonium phosphate; other nitrogen-containing organic compounds such as urea, peptone, NZ amine, meat extract, yeast extract, corn steep liquor, caseine hydrolyzates and fish meal or its digested product; and amino acids such as glycine and glutamic acid may be used.

Inorganic salts included in the medium will usually be one or more of the following: potassium dihydrogen phosphate, dipotassiumhydrogen phosphate, magnesium sulfate, magnesium phosphate, sodium chloride, ferrous sulfate, manganese sulfate, zinc sulfate and calcium carbonate.

In addition, it is preferred in productivity of uricase to add an appropriate amount of mixture of nucleic acids and/or uric acid which may serve as an inducer of the uricase gene expression. If necessary and desired, specific nutrients such as amino acids, nucleic acids and vitamins, required for its growth may be supplemented to the culture medium in appropriate amounts.

Culturing is carried out at 25°–37° C. for 1-24 hours, under the aerobic conditions by shaking or by aeration and agitation. Preferably, the pH of the culture is maintained around neutral, e.g. by the addition of ammonia, urea, or sodium hydroxide solution.

At the end of the culture, the accumulated intracellular uricase can be recovered from the cultured cells in a conventional manner. For this purpose, the culture cells are harvested by centrifugation, thoroughly washed and then disrupted by ultrasonic oscillation. The disrupted cellular product thus obtained is then centrifuged to obtain a supernatant and the supernatant is subjected to anion-exchange chromatography or hydrophobic chromatography to recover the purified enzyme.

The partial amino acid sequence of the uricase thus obtained can be, and has been determined by a peptide sequencer and that information can be used to synthesize the oligonucleotides which are to be used as probes and primers in the subsequent isolation of the uricase gene.

The titer of uricase obtained in accordance with the present invention is determined by measuring the decrease in absorption of uric acid in the ultraviolet region (293 nm). The purified enzyme is suspended in 3 ml of a reaction solution comprising 50 mM of a borate buffer solution (pH 8.5) and 125 μM uric acid (hereafter referred to as "reaction solution A"), so as to make the uricase concentration to be approximately 150 ng/ml, and the resulting mixture is incubated at 25° C. for 3 minutes. The change (ΔOD) in the absorption at wavelength 293 nm caused by the reaction is measured, and the titer (U) of uricase is calculated by the following equation. One unit is defined as the activity of the enzyme which decomposes 1 μmole of uric acid in one minute, under the above-mentioned condition.

$$U = \frac{\Delta OD \times 3 \times (\text{dilution factor of the enzyme solution})}{12.6 \times 3}$$

(the constant 12.6 is the millimole molecular extinction coefficient of uric acid)

As the amount of the uricase produced by the above method is relatively small, a recombinant plasmid-carrying *Escherichia coli* strain having a high expression activity for the enzyme has been constructed and represents a separate aspect of the present invention. The fundamental operations required for the molecular cloning and sequencing of a foreign gene in *Escherichia coli* are known and are described in detail in Molecular Cloning (1982), Cold Spring Harbor Laboratory.

Basically that procedure involves the construction, by polymerase chain reaction (PCR), of a DNA probe specific to the uricase gene and then using that probe to screen a gene bank of Cellulomonas chromosomal DNA prepared in *Escherichia coli*, by colony hybridization so as to identify an *Escherichia coli* colony containing the uricase gene, and using that colony to amplify the uricase gene by PCR.

The procedure is described hereinafter in more detail.

The N-terminal amino acid sequence of the purified uricase obtained by culturing a microorganism belonging to the genus Cellulomonas, as described above and the N-terminal amino acid sequences of various lysyl peptidase-digested fragments of that purified uricase are determined by first desalting the purified enzyme or lysyl-peptidase-digested fragments by reverse phase HPLC (column: YMC-AM312 manufactured by YMC Co., 0.1% trifluoroacetic acid (TFA)-acetonitrile gradient elution), and then subjecting the desalted purified enzyme or fragments to sequence determination on a Model 470A/120A protein sequencer (manufactured by Applied Biosystems Co.).

The N-terminal sequence data can then be used to synthesize DNA oligomers in a known manner to be used subsequently as primers in the PCR amplification of the uricase gene or probe for the uricase gene cloning from isolates of chromosomal DNA. Chromosomal DNA isolates of a uricase-producing microorganism of the genus Cellulomonas are obtained by conventional DNA isolation methods for example, the phenol method described in Biochim. Biophys. Acta, 72, 619–629, 1963. The purified chromosomal DNA isolate is then amplified by PCR using the synthesized oligonucleotide probes as primers so as to obtain an amplified DNA fragment containing at least a part of the uricase gene. The amplified DNA fragment is then ligated into a plasmid vector (pUC19, etc.), and an appropriate host such as *Escherichia coli* DH5α, described in Focus, 8, 9, 1986, is transformed with that vector e.g. by the method of Cohen et al. as described in Proc. Natl. Acad. Sci. U.S.A., 69, 2110, 1972. Using that transformant a recombinant plasmid can be isolated by conventional methods, such as the method described in "Molecular Cloning" already referred to. From that plasmid the nucleotide sequence of the inserted DNA fragment can be determined by the dideoxy method, as described in Science, 214, 1205–1210, 1981 and Gene, 19, 269–276, 1982, and checked for accuracy against the known N-terminal amino acid sequence of the purified uricase. The DNA insert can then be digested with appropriate restriction enzymes to provide a digested fragment for use as a probe in the final cloning of the uricase gene.

For this final purpose chromosomal DNA derived from a uricase-producing microorganism of the genus Cellulomonas is digested with appropriate restriction enzymes such as ScaI, and the resulting fragments ligated into a suitable DNA vector. Then, a mixture of the various recombinant molecules containing the uricase gene is used to transform *Escherichia coli* DH5α according to the method of Cohen et al., forming an *Escherichia coli* gene bank. That gene bank is then screened by colony hybridization using the above described probe, to identify positive *Escherichia coli* clones.

Each of the positive *Escherichia coli* clones is then cultured in an LB medium (pH 7.5) comprising 1% trypton, 0.5% yeast extract and 1% sodium chloride. The cells are collected by centrifugation and thoroughly washed. The resulting cells are disrupted by ultrasonication and the disrupted cellular material is centrifuged to obtain a cell-free extract. The uricase titer of the cell-free extract is determined by the above described method and the clones possessing high levels of uricase activity are selected as transformants containing the uricase gene. From those selected transformants the recombinant plasmid containing the uricase gene can be isolated and digested with HindIII and EcoRI. The nucleotide sequence of the HindIII-EcoRI cleaved DNA fragment is then determined, to confirm that it contains an open reading frame corresponding to the previously determined N-terminal amino acid sequence of the purified uricase. Thus, it is confirmed that the uricase gene has been cloned in the recombinant plasmid.

Possible cloning vectors include, but are not limited to, plasmid vectors, which, of course, must be autonomously replicable in the host cells used. For *Escherichia coli*, suitable plasmid vectors include, but are not limited to, high copy plasmids such as pBR322 (GENE, 2, 95, 1977), pUC19 (GENE, 33, 103, 1985) and pTrS33 (Japanese Published Unexamined Patent Application No. 227075/90).

It is, of course possible, and within the scope of the invention to introduce the uricase gene into other bacteria, besides *Escherichia coli* and using host vector systems appropriate to those other bacteria and to use those other bacteria for the subcloning of the gene. Also after subcloning, the sub-cloned uricase gene can be introduced into microorganisms other than *Escherichia coli* for final expression of the enzyme and using the appropriate expression vectors.

A large number of host-vector systems known in the art can be used, for example, host-vector systems of the genus Serratia as well as those of Corynebacterium, Brevibacterium, Pseudomonas and Bacillus.

Figure 3:
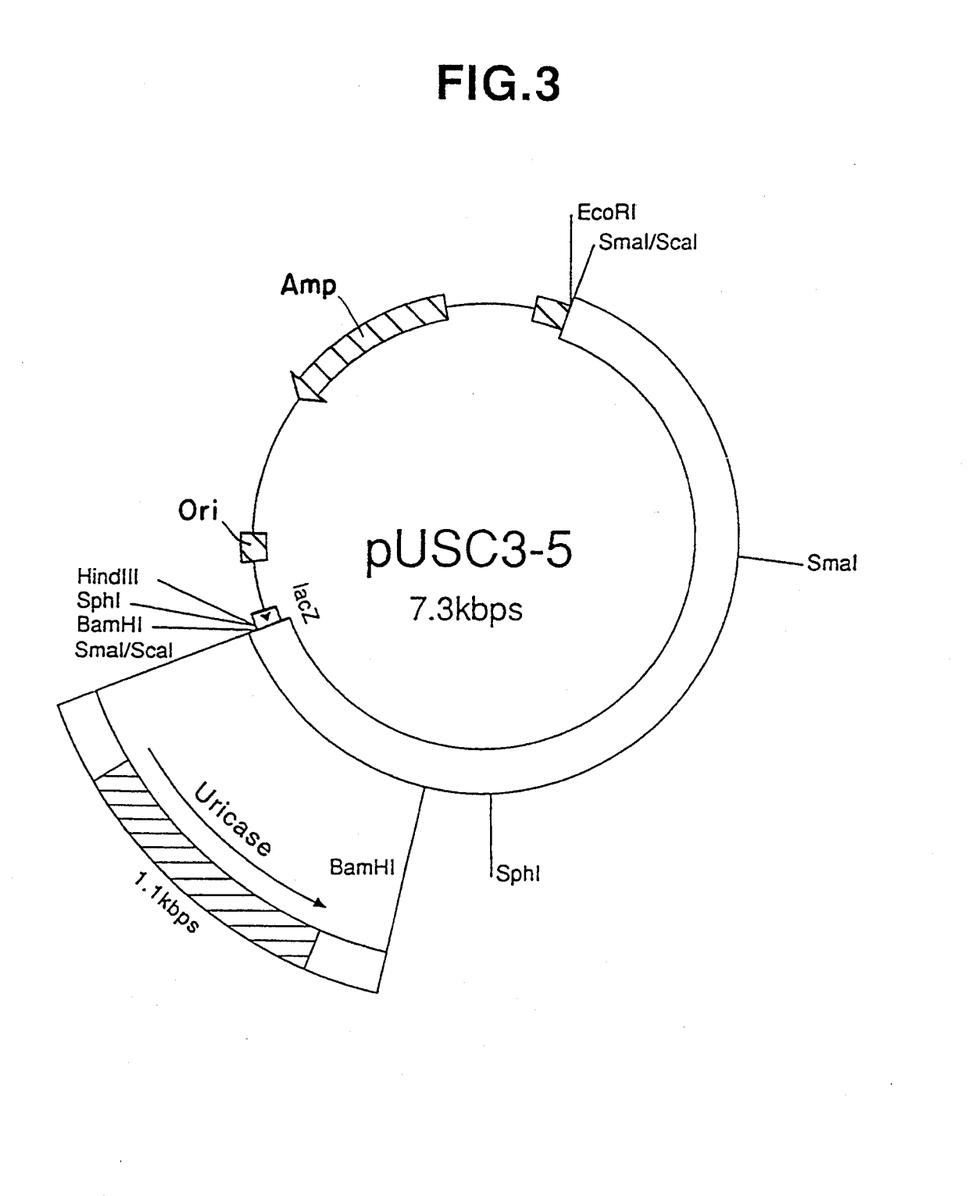
FIG. 3 is a restriction map of plasmid pUSC3-5 containing a DNA coding for uricase, isolated from Cellulomonas flavigena SK-4. In the Figure, the uricase gene is indicated by the open box portion, and the gene is transcribed in the direction from the HindIII site to the BamHI site.

The above described plasmid pUSC3-5 containing the uricase gene, cloned as described above, is illustrated in FIG. 3. The nucleotide sequence of the structure gene contained in pUSC3-5 is as set out in the Sequence Listing by SEQ ID NO: 2.

Figure 1:
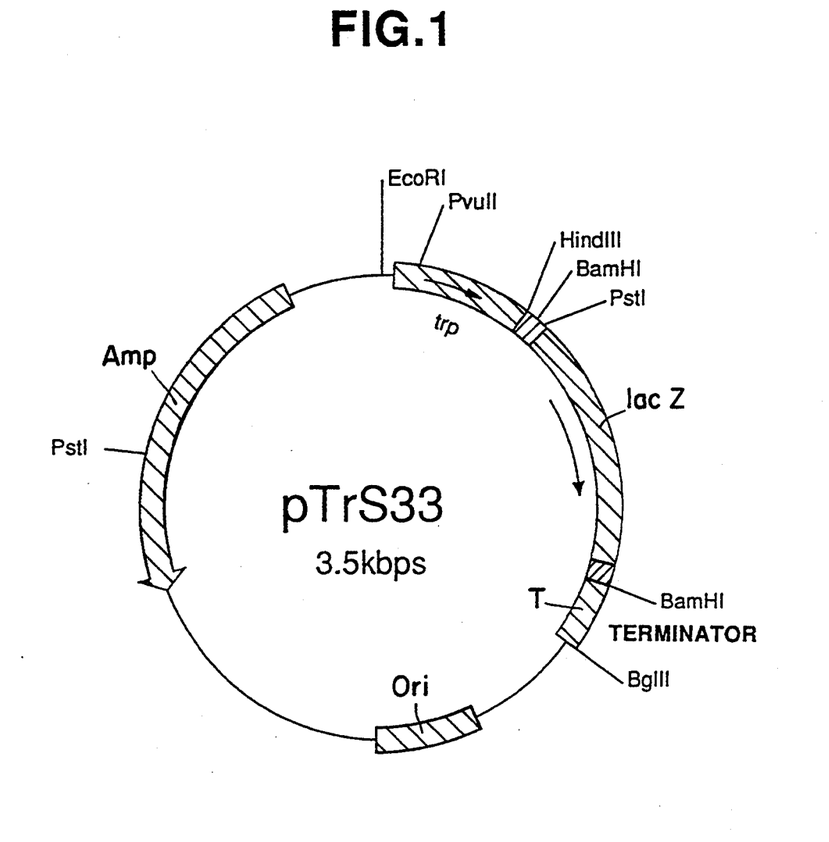
FIG. 1 is a restriction map of vector plasmid pTrS33.
Figure 4:
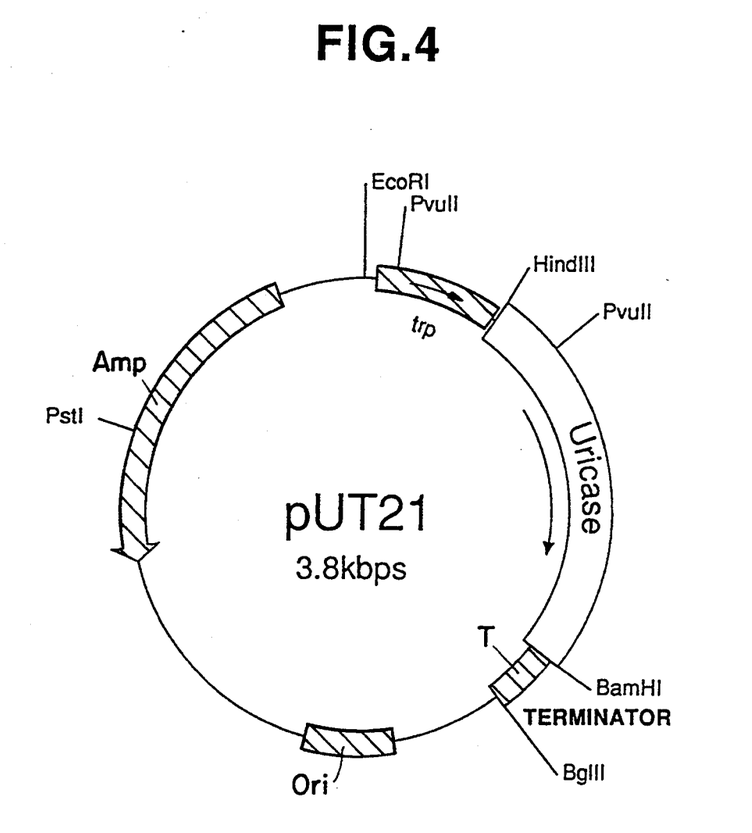
FIG. 4 is a restriction map of a uricase expression plasmid pUT21 which contains the original uricase structure gene.

As the uricase gene expression plasmid, an ATG vector such as pTrS33 (FIG. 1), can be used. In that vector gene expression is regulated by the *Escherichia coli* trpL promoter and the SD sequence. In order to ligate the uricase gene into pTrS33 PCR-derived HindIII and BamHI sites are provided at opposite ends of the gene. The resultant uricase expression plasmid pUT21 is illustrated in FIG. 4.

Figure 5:
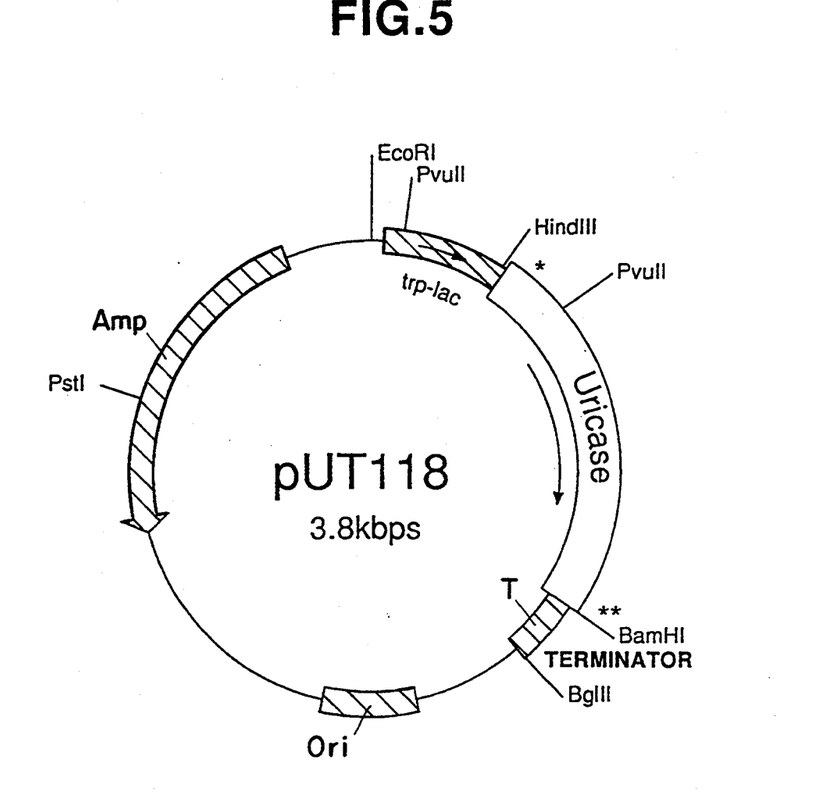
FIG. 5 is a restriction map of an efficient uricase expression plasmid pUT118 which contains a modified DNA coding for uricase. In the Figure, * denotes that the codon AGC for the second amino acid (Ser) from the N-terminal has been replaced by TCT; the third nucleotide G of the codon for the third amino acid (Thr) from the N-terminal has been replaced by T; the third nucleotide C of the codon for the fourth amino acid (Thr) from the N-terminal has been replaced by T; the third nucleotide C of the codon for the fifth amino acid (Thr) from the N-terminal has been replaced by T.

In order to improve efficiency of uricase gene expression, parts of the structure gene located downstream from the *Escherichia coli* tryptophan promoter can be altered provided that the amino acid encoding sequence is unchanged. A highly efficient expression plasmid, pUT118, which has been modified in this way is illustrated in FIG. 5. This contains the modified DNA, uricase encoding DNA sequence as defined in the Sequence Listing by SEQ ID NO: 13.

When used to transform an appropriate host cell such as *Escherichia coli*, pUT118 provides a host-vector system capable of expressing uricase in high yield.

Expression transformants according to the invention may be cultured by conventional bacterial culture methods to provide intracellular uricase in high yield. That uricase may be extracted from the cells by conventional methods e.g. by disrupting the cells to release the uricase, centrifuging and subjecting the supernatant to chromatographic separation to recover the purified enzyme. The preferred expression transformants is *Escherichia coli* DH5α transformed with plasmid pUT118. That transformant *Escherichia coli* DHUT118, has been deposited with the Fermentation Research Institute, the Agency of Industrial Science and Technology of Japan as FERM BP-3642 as of Nov. 5, 1991 under the conditions of the Budapest Treaty.

The amino acid sequence of the purified enzyme prepared from *Escherichia coli* DHUT118 has been determined by subjecting the purified enzyme, after desalting by reverse phase HPLC (YMC-AM312, 0.1% TFA-acetonitrile gradient elution), to analysis on a Model 470A/120A protein sequencer (manufactured by Applied Biosystems Co.). The determined sequence of N-terminal 22 amino acid residues corresponds to the deduced amino acid sequence, from the nucleotide sequence SEQ ID NO: 2, save that the first amino acid residue, the methionine residue, has been processed. Digestion of the enzyme with lysyl endopeptidase produces two peptides, one having an amino acid sequence corresponding to the segment from the 169 serine residue to the 183 threonine residue of SEQ ID NO: 1; and the other having a sequence corresponding to that of the segment from the 243 alanine residue to the 254 isoleucine residue of SEQ ID NO: 1 (referred to as Amino Acid Sequence A).

The invention is illustrated by the following representative examples.

EXAMPLE 1

Production of Uricase by *Cellulomonas flavigena* SK-4 (FERM BP-1575)

*Cellulomonas flavigena* SK-4 was inoculated into 300 ml of a culture medium (pH 7.2) comprising 1.0% peptone, 1.0% corn steep liquor, 0.5% Sanyo nucleic acid (made by Sanyo Kokusaku Pulp Co.), 0.5% meat extract, 0.3% yeast extract, 0.7% sucrose, 0.05% $MgSO_4 \cdot 7H_2O$ and 0.05% $FeSO_4 \cdot 7H_2O$, in an Erlenmeyer flask, and cultured with shaking at 30° C. for 16 hours. Then a portion of the resulting culture was centrifuged to obtain approximately 10 g of wet cells. The cells were suspended in 100 ml of a buffer (50 mM boric acid—sodium carbonate—potassium chloride buffer, pH 8.5; hereafter referred to as buffer A), and disrupted with an ultrasonicator (Branson Co.). The sonicated suspension was centrifuged and 100 ml of a supernatant was obtained. The supernatant was charged into an HPA-75 column (manufactured by Mitsubishi Kasei Co.; highly porous type strongly basic anion exchange resin) which had been previously equilibrated with buffer A. The column was washed with 5 column volumes of buffer A which contained 0.5M ammonium acetate. Then the uricase active fraction was eluted with 5 column volumes of buffer A which contained 0.3M ammonium sulfate. After dialyzing the uricase active fraction against buffer A, ammonium sulfate was added thereto to a final concentration of 1.1M, and the pH was adjusted to 8.5 with a potassium hydroxide solution. The resulting mixture was charged into a Butyl Toyo Pearl 650C column (manufactured by To-so Co.) which had been previously equilibrated with buffer A containing 1.1M ammonium sulfate (referred to as initiation buffer A-1), and washed with an excess amount of initiation buffer A-1. The protein was eluted with a linear gradient of 1.1 to 0M ammonium sulfate in the buffer A, and the uricase active fractions were saved. The uricase active fractions were combined and dialyzed against buffer A for desalting. 100 U of uricase were finally recovered.

The N-terminal amino acid sequences of the purified uricase thus obtained and one of the lysylpeptidase-digested fragments from the purified enzyme were analyzed to provide the data necessary to synthesize DNA oligomers corresponding to those amino acid sequences. Digestion of the purified enzyme with lysylendopeptidase (product by Wako Chem. Co.) was carried out in 4M urea, 0.1M Tris-HCl buffer (pH 9) at 37° C. for 4 hours. The N-terminal amino acid sequences were determined, after desalting the samples (about 3 μg of the purified enzyme or about 10 μg of the lysylpeptidase-digested sample) by reverse phase HPLC (YMCAM 312, 0.1% TFA-acetonitrile gradient elution), on a Model 470A/120A protein sequencer (manufactured by Applied Biosystems Co.). It was found that the N-terminal amino acid sequence of the purified enzyme was the same as $^2$Ser~$^{23}$Gly shown in SEQ ID NO: 1. It was also found that the N-terminal amino acid sequence of the lysylpeptidase-digested fragments from the purified enzyme was the same as $^{243}$Ala~$^{254}$Ile (Amino Acid Sequence A) shown in SEQ ID NO: 1.

EXAMPLE 2

Isolation of Chromosomal DNA of *Cellulomonas flavigena* SK-4

Approximately 15 g of the wet cells of *Cellulomonas flavigena* SK-4 obtained in Example 1 were suspended in 120 ml of a 20 mM Tris buffer solution (pH 7.5) containing 2 mM EDTA. To the suspension was added 15 ml of a lysozyme solution prepared by dissolving 20 mg/ml lysozyme in a 20 mM Tris buffer (pH 7.5) containing 2 mM EDTA. The resulting suspension was allowed to stand at 30° C. for 1 hour. Then 15 ml of a 20% sodium lauryl sulfate solution were added to the mixture, followed by gentle stirring. Next, 150 ml of phenol, saturated with a 10 mM Tris buffer solution (pH 7.5) containing 1 mM EDTA, were added to the mixture, followed by thorough stirring. The resulting solution was then centrifuged, and 150 ml of the aqueous layer saved. That extraction procedure was repeated three times. After the third extraction, 15 ml of 2.5M sodium acetate solution were added to 150 ml of the extracted aqueous solution followed by 300 ml of ethanol. The resulting chromosomal DNA precipitate was wound around a glass rod and dried. The dried DNA was dissolved in 30 ml of a 10 mM Tris buffer solution (pH 7.5) containing 1 mM EDTA. RNase (ribonuclease) was added to the solution to a concentration of 50 μg/ml, and the mixture was allowed to stand at 37° C. for 30 minutes. The extraction procedure with phenol, as described above, was then repeated four more times. At the end of that extraction 3 ml of 2.5M potassium acetate solution and 60 ml of ethanol were added to the extracted aqueous solution and the solution was allowed to stand at −20° C. for 16 hours. The chromosomal DNA precipitate was separated by centrifuging and the resulting DNA pellet was washed with 70% ethanol solution and dried. The purified chromosomal DNA pellet was then suspended in a 10 mM Tris buffer solution (pH 7.5) containing 1 mM of EDTA, for storage at −20° C.

EXAMPLE 3

Synthesis of a Probe for Cloning the Uricase Gene

1) Amplification of a probe DNA fragment

Based on the amino acid sequence data obtained in Example 1, a 5'-end primer having the nucleotide sequence SEQ ID NO: 5 corresponding to the amino acid sequence near the N-terminal, and a 3'-end primer having the nucleotide sequence SEQ ID NO: 6 (corresponding to the amino acid sequence A) were designed and synthesized by the amidide phosphate solid phase synthesis method (S. L. Beaucage et. al., Tetrahedron Lett., 12, 1859, 1981), using a DNA automatic synthesizer 380A (manufactured by Applied Biosystems Co.).

Those two primers were then used to amplify 1 ng of the chromosomal DNA obtained in Example 2 by PCR. The PCR was carried out using the following reaction cycle repeated 30 times: 94° C. for 1.5 minutes, 40° C. for 2 minutes and 72° C. for 2 minutes, and using a Gene Amp DNA Amplification Reagent Kit (product by Takara Shuzo Co.). 1.0 μM of each the two primers was used in the PCR together with 200 μM each of dATP, dCTP, dGTP and dTTP. 2.5 U/100 μl of Taq DNA polymerase was used as the enzyme in the final cycle volume of 100 μl. An amplified 700 bp DNA fragment was obtained.

2) Cloning of the Probe DNA Fragment

1 μg of the DNA fragment obtained by the above PCR reaction was digested with HindIII and EcoRI in 20 μl of REact 2 buffer (1×Conc.) (pH 8.0) (product by BRL Co.). 1 μg of the vector pUC19 was also separately digested with HindIII and EcoRI. The digested DNA fragment and digested vector DNA were then each purified by extraction with phenol and precipitation with ethanol by the same method as described in Example 2. 100 ng of the purified DNA and 20 ng of the purified vector were then suspended in a solution containing a 66 mM Tris buffer solution (pH 7.6), 66 mM magnesium chloride, 10 mM DTT and 0.1 mM ATP. After adding 10 U of T4DNA ligase (product by Takara Shuzo Co.) to the resulting suspension, the suspension was allowed to stand at 14° C. for 16 hours to complete the ligation reaction and to provide a recombinant pUC19 vector containing the DNA fragment as an insert therein.

*Escherichia coli* DH5α strain was inoculated into 50 ml of an LB liquid medium in an Erlenmeyer flask, and cultured with shaking at 37° C. for 4 hours. Then the cells were collected by centrifugation (3000 rpm, 7 minutes) and suspended in 20 ml of a 50 mM calcium chloride solution at 0° C. followed by standing at 0° C. for 20 minutes. The cells were collected again by centrifugation in the same manner as above, and suspended in 40 ml of a 50 mM calcium chloride solution at 0° C. The suspension was mixed with the suspension containing the recombinant pUC19 vector as described above. The resulting mixture was allowed to stand at 0° C. for 10 minutes. After heating at 42° C. for 90 seconds, the mixture was spread on an LB agar plate containing 100 μg/ml ampicillin and 20 μg/ml 5-bromo-4-chloroindolyl-β-galactoside (Xgal). The plate was then kept at 37° C. for approximately 24 hours.

Some of the white colonies thus grown were cultured independently in an LB liquid culture medium and the cells were collected. The plasmid DNA was extracted by a conventional means as described in Molecular Cloning, and the nucleotide sequence of the cloned DNA fragment was determined by the dideoxy method. The nucleotide sequence was found to correspond to the amino acid sequence SEQ ID NO: 1, and the cloned DNA fragment was found to be suitable as a probe for the cloning of the uricase gene.

EXAMPLE 4

Cloning of the Uricase Gene by Colony Hybridization

1) Preparation of the Gene Bank

ScaI was added to 20 μl of REact 6 buffer (1×Conc.) (pH 7.4) (product by BRL Co.) containing 1 μg of the chromosomal DNA, prepared as in Example 2, for digestion. Separately, SmaI was added to 20 μl of REact 4 buffer (1×Conc.) (pH 7.4) containing 1 μg of the vector pUC19 for digestion. A 1M Tris buffer solution (pH 8.0) and 10 U of alkaline phosphatase were added to 20 μl of the SmaI-digested solution containing the vector pUC19. The mixture was then heated at 65° C. for 1 hour. The digested chromosomal DNA and vector DNA were purified by extraction with phenol and precipitation with ethanol as described in Example 2. One hundred nanograms of the purified chromosomal DNA and 20 ng of the purified vector DNA were then suspended in 30 μl of a 66 mM Tris buffer solution (pH 7.6) containing 66 mM of magnesium chloride, 10 mM of DTT and 0.1 mM of ATP. Ten units of T4DNA ligase (product by Takara Shuzo Co.) were added to the mixture followed by reaction at 14° C. for 16 hours. Both of DNAs were ligated to each other so as to obtain a variety of recombinant DNA molecules.

2) Colony Hybridization

One microgram of the probe DNA, prepared in paragraph (2) of Example 3, was labelled with an enzyme using an enzyme labelling and detection kit (DIG-ELISA method, Catolog No. 1093657; Berlinger Manheim Co.). The labelled DNA was used as a uricase gene detection probe.

*Escherichia coli* DH5α strain was cultured in 50 ml of an LB liquid medium in an Erlenmeyer flask, and cultured with shaking at 37° C. for 4 hours. The cells were then collected by centrifugation (3000 rpm, 7 minutes) and suspended in 20 ml of a 50 mM calcium chloride solution at 0° C. followed by standing at 0° C. for 20 minutes. The cells were collected again by centrifugation in the same manner as above, and then suspended in 40 ml of a 50 mM calcium chloride solution at 0° C. The suspension was mixed with 10 mM Tris buffer solution (pH 7.5) containing 1 mM EDTA and the recombinant DNA mixtures as obtained above. The mixture was allowed to stand at 0° C. for 10 minutes. After heating at 42° C. for 90 seconds, the mixture was spread on an LB agar plate medium containing 100 μg/ml ampicillin and 20 μg/ml Xgal. The plate was then kept at 37° C. for approximately 24 hours.

A membrane filter, Nytran NY13N (product by Schleicher & Scheull Co.) was placed on the colonies and immediately peeled off. The membrane was then placed upside down on another LB agar plate medium containing 100 μg/ml ampicillin, and was kept at 37° C. for approximately 12 hours. The membrane, now carrying the ampicillin resistant colonies was then peeled off and placed on a filter paper containing 0.5M NaOH for 10 minutes, followed by 5 minutes on a filter paper containing 0.5M of a Tris buffer solution (pH 7.3), 5 minutes on a filter paper containing 0.5M of a Tris buffer solution (pH 7.3) containing 0.5M of NaCl, and finally on a filter paper containing 2×SSC (0.3M of NaCl, 0.03M of tripotassium citrate, pH 7.0). Following that last treatment, the membrane filter was heated at 80° C. for approximately 3 hours and then screened using the above mentioned enzyme-labelled uricase gene detection probe. By this procedure repeated several times 4 positive clones (transformants) were eventually selected out of approximately 10,000 colonies.

3) Verification of the Cloned Gene

Each of the positive clones (transformants) was inoculated into 10 ml of an LB culture medium containing 100 μg/ml ampicilin in a test tube, and cultured with shaking at 37° C. for approximately 24 hours. The cells were then collected from the culture by centrifugation, and a cell-free extract was prepared by sonification of the harvested cells, centrifugation of the disrupted cells and recovery of the supernatant. The uricase activity of the supernatant was determined and found to be 2-4 U per mg-protein. Plasmid DNA was isolated from the harvested cells by the method mentioned above and digested in an amount of 1 μg in 20 μl of REact 2 buffer (1×Conc.) (pH 8.0) containing HindIII and EcoRI. The resulting reaction mixture was then subjected to electrophoresis using a 0.8% agarose gel containing 0.5 μg/ml ethidium bromide. The length of the HindIII-EcoRI cleaved fragment was measured and the fragment was transferred, by conventional means, as described in Molecular Cloning, to a membrane filter such as Nytran. The membrane filter was then processed with the above mentioned enzyme-labelled uricase gene detection probe. Positive results were obtained in all cases.

One of the positive transformants was selected, and the plasmid was isolated from the transformant by the same method as described above. The nucleotide sequence of the cloned DNA fragment was determined. It was found to contain an open reading frame corresponding to the amino acid sequence SEQ ID NO: 1. The nucleotide sequence of the uricase structure gene contained in the plasmid is illustrated in SEQ ID NO: 2.

The recombinant plasmid was named pUSC3-5. The restriction map of plasmid pUSC3-5 is given in FIG. 3.

EXAMPLE 5

Construction of an Efficient Uricase Expression Plasmid and Introduction of the Plasmid into an *Escherichia coli*

In order to introduce a tryptophan promoter sequence and an SD sequence of trpL into the upstream of the uricase structure gene obtained in Example 4, a 5'-end primer SEQ ID NO: 7 and a 3'-end primer SEQ ID NO: 8 were synthesized. Utilizing these primers, a PCR reaction was carried out in the same manner as described in Example 3, Step 1 with an EcoRI-digested DNA fragment of pUSC3-5 obtained by digesting the plasmid pUSC3-5 with EcoRI in REact 3 buffer (1×Conc.) (pH 8.0) containing 1 μg of the recombinant plasmid.

To 20 μl of REact 2 buffer (1×Conc.) (pH 8.0) containing 1 μg of the amplified DNA fragment obtained from the above PCR reaction were added HindIII and BamHI. To 20 μl of REact 2 buffer (1×Conc.) (pH 8.0) containing 1 μg of vector pTrS33 were also added HindIII and BamHI. The digested DNA fragment and the digested vector DNA were then ligated to each other to form the plasmid pUT21 (FIG. 4).

*Escherichia coli* DH5α was then transformed with pUT21 by the method described in Molecular Cloning to give the transformant *Escherichia coli* {DH5α (pUT21)}. The transformant was cultured by the method described in Example 6, and the enzyme was recovered from the cultured cells. The amount of the uricase recovered was 50 U/ml.

In a separate series of experiments and in order to change the SD sequence of vector pTrS33 into the SD sequence of lacZ, the 5'-end primer SEQ ID NO: 9 and the 3'-end primer SEQ ID NO: 10 were synthesized.

PstI was added to REact 2 buffer (1×Conc.) (pH 8.0) containing 1 μg of recombinant plasmid pTrS33 for digestion.

Utilizing these primers, a PCR reaction was carried out in the same manner as described in Example 3, Step 1) using a PstI-digested fragment of pTrS33 as the template.

Figure 2:
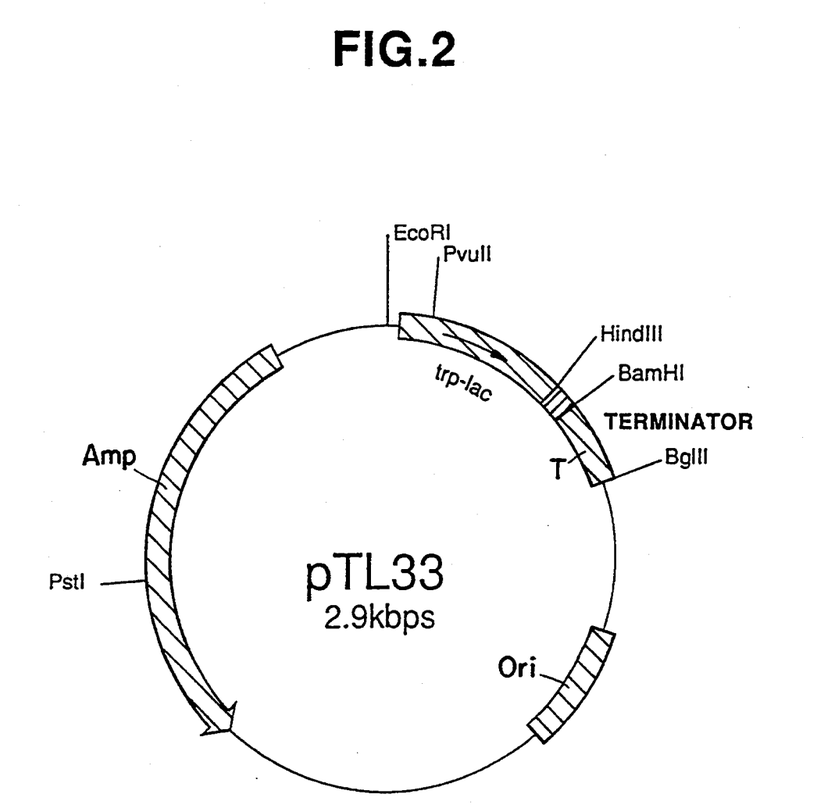
FIG. 2 is a restriction map of vector plasmid pTL33.

To 20 μl of REact 2 buffer (1×Conc.) (pH 8.0) containing 1 μg of the amplified DNA fragment obtained from the above PCR reaction were added EcoRI and HindIII. To 20 μl of REact 2 buffer (1×Conc.) (pH 8.0) containing 1 μg of vector pTrS33 were also added EcoRI and HindIII following which the digested DNA fragment and the digested vector DNA were ligated to each other in the same manner as described in Example 3, Step 2) to form the plasmid pTL33 (FIG. 2).

In another series of experiments, silent mutations as described below were introduced into the uricase structure gene and any DNA derived from *C. flavigena* other than the structure gene when constructing more efficient uricase expression plasmids. The nucleotide sequence shown in SEQ ID NO: 3, which corresponds to the N-terminal portion of the uricase, was altered to the nucleotide sequence shown in SEQ ID NO: 4 so that no alterations in coded amino acid were caused.

For these purposes, a 5'-end primer SEQ ID NO: 11 and a 3'-end primer SEQ ID NO: 12 were synthesized. Utilizing these two primers, a PCR reaction was carried out with the EcoRI-digested fragment of pUT21 as a template in the same manner as described in Example 3, Step 1). 1 μg of the DNA fragment obtained from the PCR reaction in 20 μl of REact 2 buffer (1×Conc.) (pH 8.0) was digested with HindIII and BamHI. 1 μg of vector plasmid pTL33 in 20 μl of REact 2 buffer ((1×Conc.) (pH 8.0) was also digested with HindIII and BamHI. Each of the digested DNA fragment and the digested Vector DNA was then ligated in the same manner as described in Example 3, Step 3) to form plasmid pUT118 (FIG. 5). *Escherichia coli* DH5α was then transformed with pUT118 in the same manner as described above to form the transformant *Escherichia coli* DHUT118.

EXAMPLE 6

Uricase Production

*Escherichia coli* DHUT118 (FERM BP-3642), obtained as in Example 5, was cultured by a modified method of the high density culture method described in Biotechnology and Bioengineering, 17, 227–239, 1975. For this purpose *Escherichia coli* DHUT118 was inoculated into a seed culture medium having the following composition and cultured at 30° C. for 16 hours.

Seed culture medium composition:

3.5 g/l $KH_2PO_4$, 3.5 g/l $(NH_4)_2HPO_4$, 1.0 g/l $MgSO_4.7H_2O$, 5.0 g/l glucose, 50 g/l yeast extract, and 3 ml/l of a trace element solution (autoclaved at 120° C. for 30 minutes).

Trace element solution composition:

27 g/l $FeCl_3.6H_2O$, 2 g/l $ZnCl_2.4H_2O$, 2 g/l $CoCl_2.6H_2O$, 2 g/l $Na_2MoO_4.2H_2O$, 1 g/l $CaCl_2.2H_2O$, 1 g/l $CuCl_2$, 0.5 g/l $H_3BO_3$, and 100 ml/l of conc. HCl.

3 liters of a fermentation medium, prepared by adding 10 g of $KH_2PO_4.3H_2O$ and 5 g of $MgSO_4.7H_2O$ to 3 liters of a seed culture medium having the same composition as the above mentioned, were poured into a 7.5-liter jar fermentor, and autoclaved at 120° C. for 30 minutes. 150 ml of a 50% (W/W) glucose solution were sterilized and added to the fermentation medium in the jar fermentor followed by 500 ml of the seed culture.

Culturing was carried out at 33° C. for 24 hours under conditions of agitation (600 rpm) and aeration (3 l/min) and at a pH of 6.8 obtained by the appropriate additions of 5.5M aqueous ammonia. After 4–6 hours when the glucose concentration of the culture has dropped to 2.5% or less, aliquots of 50% (W/V) glucose solution were added so as to maintain a glucose concentration in the range 2–3%. The resulting culture has a uricase activity of 200 U/ml.

A portion of the product culture was centrifuged to obtain approximately 10 g of wet cells. The wet cells were then suspended in 100 ml of buffer A, and disrupted by ultrasonic oscillation with a Sonifier Cell Disruptor 350 (manufactured by Branson Sonic Power Co.). The sonicated suspension was then centrifuged, and 100 ml of a supernatant was obtained. Magnesium sulfate was then added to the supernatant to a final concentration of 50 mM, and after adjustment to pH 8.5 with a potassium hydroxide solution, the solution was heated at 60° C. for 30 minutes. The solution was then centrifuged, and the protein impurities, etc. were removed as a precipitate. The supernatant was charged into a DEAE Toyo Pearl 650S column (manufactured by To-So Co., diameter 2.2 cm, length 20 cm) which had been previously equilibrated with buffer A. The column was washed with an excess amount of buffer A. Then, it was eluted with a linear gradient of 0 to 0.4M NaCl in the buffer A (total volume, 800 ml). 100 ml of uricase active fractions were obtained. These were combined and dialyzed against buffer A, and ammonium sulfate was added to the dialyzed solution to a final concentration of 1.5M. The solution was adjusted to pH 8.5 with potassium hydroxide. The solution was then charged into a Butyl Toyo Pearl 650S column (manufactured by To-So Co., diameter 2.2 cm, length 20 cm) which had been previously equilibrated with buffer A containing 1.5M of ammonium sulfate (initiation buffer 2). The column was washed with an excess amount of initiation buffer 2. The protein was eluted with a linear gradient of 1.5 to 0M ammonium sulfate in buffer A (total volume, 800 ml), and 60 ml of uricase active fractions were recovered. The uricase active fractions were dialyzed against buffer A for desalting so as finally to recover 15,400 U of uricase.

The N-terminal amino acid sequences of the purified uricase and of the two fragments obtained by lysylpeptidase-digestion of the purified enzyme were determined in the same manner as described in Example 1. It was found that the N-terminal amino acid sequence of the purified enzyme was the same as $^2Ser \sim {}^{23}Gly$ shown in SEQ ID NO: 1. It was also found that the N-terminal amino acid sequences of the lysylpeptidase-digested fragments were the same as $^{169}Ser \sim {}^{183}Thr$ and $^{243}Ala \sim {}^{254}Ile$ (Amino Acid Sequence A) shown in SEQ ID NO: 1.

Further, the above mentioned desalted sample from the purified enzyme (1 nmol) was oxidized with performic acid at −4° C. for 2 hours, and concentrated to dryness under reduced pressure. The concentrate was digested with hydrazine at 95° C. for 2 hours using Hydraclub S-204 (manufactured by Ho-nen Co.). The excess hydrazine was removed under reduced pressure and the hydrazide contained in the decomposed products was reacted with benzaldehyde. The reaction product was removed by centrifuging and the supernatant subjected to amino acid analysis by the OPA-Precolumn method. Approximately 300 pmol of cysteic acid was detected. Thus, it was proved that amino acid residue at the C-terminal is cysteine. The above results indicate that the amino acid sequence of the enzyme derived from *Escherichia coli* DHUT118 coincides with the amino acid sequence which is deduced from the nucleotide sequence SEQ ID NO: 2.

Finally, in the recombinant DNA art, it is well understood that in any DNA sequence encoding a gene product non-critical substitutions, deletions or additions may be made in the sequence without materially affect the gene product expressed by that gene. Similarly, it is well understood that in any amino acid sequence representing a protein having specific properties, such as, in this case, uricase activity, non-critical substitutions, additions or deletions may likewise be made without materially affecting the activity of the protein, in this case its uricase activity.

It is to be understood therefore that the present invention is not restricted to the specific sequences identified herein as SEQ ID NOS: 1, 2 and 13 but is to be construed as covering non-critical substitutions, deletions or additions in, from or to those sequences.

What is claimed is:

1. A DNA isolate comprising a DNA fragment encoding a protein having uricase activity and the amino acid sequence SEQ ID NO: 1.

2. A DNA isolate according to claim 1, wherein the said DNA fragment is a fragment isolated from chromosomal DNA of a *Cellulomonas flavigena* SK-4.

3. A DNA isolate according to claim 1, wherein the said DNA fragment has the nucleotide sequence SEQ ID NO: 2.

4. A modified version of the DNA claimed in claim 1, wherein the modified version has the nucleotide sequence SEQ ID NO: 13.

5. A recombinant plasmid containing a DNA fragment as claimed in claim 1, capable when inserted into a host, of expressing a protein having the amino acid sequence SEQ ID NO: 1.

6. A transformant which contains a recombinant plasmid according to claim 5 and which is capable of expressing a protein having the amino acid sequence SEQ ID NO: 1.

7. A process for producing uricase which comprises culturing a transformant as claimed in claim 6 in a culture medium and recovering the accumulated uricase from the culture.

8. A process according to claim 7, wherein said transformant is *Escherichia coli* {DH5α (pUT21)} or *Escherichia coli* DHUT118 (FERM BP-3642).

9. The plasmids: pUSC3-5, pUT21 and pUT118.

10. A process for producing uricase which comprises culturing, in a culture medium, *Cellulomonas flavigena* SK-4 and recovering the accumulated uricase from the culture.

* * * * *

SEQUENCE LISTING ( 1 ) GENERAL INFORMATION:

( i i i ) NUMBER OF SEQUENCES: 13

( 2 ) INFORMATION FOR SEQ ID NO: 1 :

( i ) SEQUENCE CHARACTERISTICS:
    ( A ) LENGTH: 313 amino acids
    ( B ) TYPE: amino acid
    ( C ) STRANDEDNESS: single
    ( D ) TOPOLOGY: linear ( i i ) MOLECULE TYPE:protein ( i i i ) HYPOTHETICAL: NO ( i v ) ANTI-SENSE: NO ( v ) FRAGMENT TYPE: N-terminal fragment ( v i ) ORIGINAL SOURCE:
    ( A ) ORGANISM: Cellulomonas flavigena
    ( B ) STRAIN: SK-4

( x i ) SEQUENCE DESCRIPTION: SEQ ID NO: 1:

| Met 1 | Ser | Thr | Thr | Thr 5 | Pro | Thr | Ala | Glu | Gln 10 | Pro | Ala | Ala | Thr | Gln 15 | Ser |
|---|---|---|---|---|---|---|---|---|---|---|---|---|---|---|---|
| Ser | Gly | Ala | Ile 20 | Val | Leu | Gly | Asp | Asn 25 | Gln | Trp | Gly | Lys | Ala 30 | Glu | Val |
| Arg | Leu | Val 35 | Arg | Val | Asp | Arg | Ala 40 | Thr | Pro | Arg | His | Glu 45 | Ile | Thr | Asp |
| Val | Asn 50 | Val | Ser | Ser | Gln | Leu 55 | Arg | Gly | Gly | Gln | Glu 60 | Ala | Thr | His | Leu |
| Glu 65 | Gly | Asp | Asn | Ser | Arg 70 | Cys | Val | Ala | Thr | Asp 75 | Thr | Gln | Lys | Asn | Thr 80 |
| Ile | Tyr | Ala | Phe | Ala 85 | Arg | Asp | Gly | Val | Gly 90 | Ala | Ile | Glu | Asp | Phe 95 | Ala |
| Ile | Arg | Leu | Gly 100 | Gln | His | Phe | Val | Glu 105 | Asp | Phe | Glu | Trp | Ile 110 | Glu | Gly |
| Gly | Arg | Trp 115 | Glu | Ile | Glu | Gln | Tyr 120 | Thr | Trp | Asn | Arg | Ile 125 | Glu | Thr | Ala |
| Asp | Gly 130 | Glu | His | Asp | His | Ala 135 | Phe | Val | Arg | Asn | Asn 140 | Gln | Glu | Thr | Arg |
| Thr 145 | Thr | Val | Val | Gln | Arg 150 | Asp | Gly | Asp | Glu | Val 155 | Phe | Val | Val | Ser | Gly 160 |
| Leu | Thr | Asp | Leu | Val 165 | Val | Leu | Lys | Ser | Thr 170 | Gly | Ser | Glu | Phe | His 175 | Gly |
| Phe | Pro | Arg | Asp 180 | Arg | Tyr | Thr | Thr | Leu 185 | Val | Glu | Thr | Asn | Asp 190 | Arg | Ile |
| Leu | Ala | Thr 195 | Ser | Val | Thr | Ser | Arg 200 | Trp | Arg | Tyr | Thr | Thr 205 | Thr | Asp | Val |
| Asp | Phe 210 | Asp | Ala | Val | Tyr | Ala 215 | Lys | Val | Arg | Ala | Ile 220 | Gln | Leu | Glu | Ala |

| | | | | | | | | | | | | | | |
|---|---|---|---|---|---|---|---|---|---|---|---|---|---|---|
|Phe|Ala|Thr|Thr|His|Ser|Leu|Ala|Leu|Gln|Gln|Thr|Leu|Phe|Ala|Met|
|225| | | | |230| | | |235| | | | | |240|
|Gly|Lys|Ala|Val|Leu|Glu|Ala|Ile|Pro|Glu|Ile|Ala|Glu|Ile|Lys|Phe|
| | | | |245| | | |250| | | | |255| |
|Ser|Met|Pro|Asn|Lys|His|His|Phe|Leu|Val|Asp|Leu|Ala|Pro|Phe|Gly|
| | | |260| | | |265| | | |270| | | |
|Leu|Asp|Asn|Pro|Asn|Glu|Val|Phe|Tyr|Ala|Ala|Asp|Arg|Pro|Tyr|Gly|
| | |275| | | |280| | | |285| | | | |
|Leu|Ile|Glu|Ala|Thr|Val|Gln|Arg|Glu|Gly|Glu|Pro|Ala|Glu|Pro|Arg|
| |290| | | |295| | | | |300| | | | |
|Ala|Trp|Ala|Thr|Val|Thr|Gly|Phe|Cys|
|305| | | |310| | | | |

( 2 ) INFORMATION FOR SEQ ID NO: 2:

( i ) SEQUENCE CHARACTERISTICS:
        ( A ) LENGTH: 942 base pairs
        ( B ) TYPE: nucleic acid
        ( C ) STRANDEDNESS: double
        ( D ) TOPOLOGY: linear     ( i i ) MOLECULE TYPE:Genomic DNA     ( i i i ) HYPOTHETICAL: NO     ( i v ) ANTI-SENSE: NO     ( v i ) ORIGINAL SOURCE:
        ( A ) ORGANISM: Cellulomonas flavigena
        ( B ) STRAIN: SK-4

( x i ) SEQUENCE DESCRIPTION: SEQ ID NO: 2:

| | | | | | |
|---|---|---|---|---|---|
|ATGAGCACGA|CCACCCCGAC|CGCCGAGCAG|CCGGCGGCCA|CGCAGAGCAG|CGGGGCCATC 60|
|GTCCTGGGCG|ACAACCAGTG|GGGCAAGGCG|GAGGTGCGCC|TCGTGCGCGT|CGACCGCGCC 120|
|ACGCCTCGCC|ACGAGATCAC|GGACGTCAAC|GTCTCCTCGC|AGCTGCGGGG|CGGGCAGGAG 180|
|GCCACGCACC|TGGAGGGCGA|CAACTCCCGG|TGCGTCGCCA|CCGACACCCA|GAAGAACACG 240|
|ATCTACGCCT|TCGCCCGCGA|CGGCGTCGGC|GCGATCGAGG|ACTTCGCGAT|CCGCCTCGGT 300|
|CAGCACTTCG|TCGAGGACTT|CGAGTGGATC|GAGGGCGGCC|GCTGGGAGAT|CGAGCAGTAC 360|
|ACCTGGAACC|GCATCGAGAC|CGCCGACGGC|GAGCACGACC|ACGCGTTCGT|CCGGAACAAC 420|
|CAGGAGACGC|GCACGACGGT|CGTCCAGCGC|GACGGCGACG|AGGTCTTCGT|CGTCTCGGGA 480|
|CTCACGGACC|TCGTCGTGCT|CAAGTCCACC|GGCTCGGAGT|TCCACGGGTT|CCCGCGCGAC 540|
|CGCTACACGA|CGCTCGTGGA|GACCAACGAC|CGCATCCTCG|CGACGTCGGT|CACCTCGCGG 600|
|TGGCGCTACA|CGACCACCGA|CGTCGACTTC|GACGCCGTGT|ACGCGAAGGT|CCGCGCGATC 660|
|CAGCTCGAGG|CGTTCGCGAC|GACCCACTCC|CTCGCGCTCC|AGCAGACGCT|GTTCGCGATG 720|
|GGCAAGGCGG|TCCTCGAGGC|GATCCCGGAG|ATCGCCGAGA|TCAAGTTCTC|GATGCCGAAC 780|
|AAGCACCACT|TCCTCGTGGA|CCTCGCGCCG|TTCGGCCTCG|ACAACCCGAA|CGAGGTCTTC 840|
|TACGCGGCCG|ACCGCCCGTA|CGGCCTCATC|GAGGCGACGG|TCCAGCGCGA|GGGCGAGCCG 900|
|GCCGAGCCGC|GCGCCTGGGC|GACCGTCACC|GGGTTCTGCT|GA| 942|

( 2 ) INFORMATION FOR SEQ ID NO: 3:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear     ( i i ) MOLECULE TYPE:Genomic DNA (i i i) HYPOTHETICAL: NO (i v) ANTI-SENSE: YES (x i) SEQUENCE DESCRIPTION: SEQ ID NO: 3:

ATGAGCACGA CCACCCCG                                                                 18

(2) INFORMATION FOR SEQ ID NO: 4 :

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (i i) MOLECULE TYPE:Other nucleic acid
        SYNTHETIC DNA (i i i) HYPOTHETICAL: NO (i v) ANTI-SENSE: NO (x i) SEQUENCE DESCRIPTION: SEQ ID NO: 4:

ATGTCTACTA CTACTCCG                                                                 18

(2) INFORMATION FOR SEQ ID NO: 5 :

(i) SEQUENCE CHARACTERISTICS:
        (A) LENGTH: 31 base pairs
        (B) TYPE: nucleic acid
        (C) STRANDEDNESS: single
        (D) TOPOLOGY: linear     (i i) MOLECULE TYPE:Other nucleic acid
        SYNTHETIC DNA (i i i) HYPOTHETICAL: NO (i v) ANTI-SENSE: NO (x i) SEQUENCE DESCRIPTION: SEQ ID NO: 5:

GGGAATTCGG ATCCGGSGCS ATCGTSCTSG G                                                  31

(2) INFORMATION FOR SEQ ID NO: 6 :

(i) SEQUENCE CHARACTERISTICS:
        (A) LENGTH: 41 base pairs
        (B) TYPE: nucleic acid
        (C) STRANDEDNESS: single
        (D) TOPOLOGY: linear     (i i) MOLECULE TYPE:Other nucleic acid
        SYNTHETIC DNA (i i i) HYPOTHETICAL: NO (i v) ANTI-SENSE: NO (x i) SEQUENCE DESCRIPTION: SEQ ID NO: 6:

AAAAGCTTCT GCAGGATCTC SGCGATCTCS GGGATSGCCT C                                       41

(2) INFORMATION FOR SEQ ID NO: 7 :

(i) SEQUENCE CHARACTERISTICS:
        (A) LENGTH: 40 base pairs
        (B) TYPE: nucleic acid
        (C) STRANDEDNESS: single
        (D) TOPOLOGY: linear     (i i) MOLECULE TYPE:Other nucleic acid
        SYNTHETIC DNA (i i i) HYPOTHETICAL: NO (iv) ANTI-SENSE: NO (xi) SEQUENCE DESCRIPTION: SEQ ID NO: 7:

GGGAAAGCTT ATGAGCACGA CCACCCCGAC CGCCGAGCAG 40

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear     (ii) MOLECULE TYPE: Other nucleic acid
        SYNTHETIC DNA (iii) HYPOTHETICAL: NO (iv) ANTI-SENSE: NO (xi) SEQUENCE DESCRIPTION: SEQ ID NO: 8:

CGACTCTAGA GGATCCTCCG CGGTCGGGCA GGGCGC 36

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear     (ii) MOLECULE TYPE: Other nucleic acid
        SYNTHETIC DNA (iii) HYPOTHETICAL: NO (iv) ANTI-SENSE: NO (xi) SEQUENCE DESCRIPTION: SEQ ID NO: 9:

CTTCAAGAAT TCTCATGTTT GACAGCTTAT CATCG 35

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear     (ii) MOLECULE TYPE: Other nucleic acid
        SYNTHETIC DNA (iii) HYPOTHETICAL: NO (iv) ANTI-SENSE: NO (xi) SEQUENCE DESCRIPTION: SEQ ID NO: 10:

CTCATAAGCT TTTCCTGTAT AGGTCGAGTT GCGTAC 36

(2) INFORMATION FOR SEQ ID NO: 11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear     (ii) MOLECULE TYPE: Other nucleic acid
        SYNTHETIC DNA (iii) HYPOTHETICAL: NO (iv) ANTI-SENSE: NO ( x i ) SEQUENCE DESCRIPTION: SEQ ID NO: 11:

GGGAAAGCTT ATGTCTACTA CTACTCCGAC CGCCGAGCAG    40

( 2 ) INFORMATION FOR SEQ ID NO: 12 :

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE:Other nucleic acid
        SYNTHETIC DNA     ( i i i ) HYPOTHETICAL: NO     ( i v ) ANTI-SENSE: NO     ( x i ) SEQUENCE DESCRIPTION: SEQ ID NO: 12:

CGTCGGATCC TTATTAGCAG AACCCGGTGA C    31

( 2 ) INFORMATION FOR SEQ ID NO: 13 :

( i ) SEQUENCE CHARACTERISTICS:
        ( A ) LENGTH: 945 base pairs
        ( B ) TYPE: nucleic acid
        ( C ) STRANDEDNESS: double
        ( D ) TOPOLOGY: linear     ( i i ) MOLECULE TYPE:Genomic DNA     ( i i i ) HYPOTHETICAL: NO     ( i v ) ANTI-SENSE: NO     ( v i ) ORIGINAL SOURCE:
        ( A ) ORGANISM: Cellulomonas flavigena
        ( B ) STRAIN: SK-4

( x i ) SEQUENCE DESCRIPTION: SEQ ID NO: 13:

```
ATGTCTACTA CTACTCCGAC CGCCGAGCAG CCGGCGGCCA CGCAGAGCAG CGGGGCCATC     60
GTCCTGGGCG ACAACCAGTG GGGCAAGGCG GAGGTGCGCC TCGTGCGCGT CGACCGCGCC    120
ACGCCTCGCC ACGAGATCAC GGACGTCAAC GTCTCCTCGC AGCTGCGGGG CGGGCAGGAG    180
GCCACGCACC TGGAGGGCGA CAACTCCCGG TGCGTCGCCA CCGACACCCA GAAGAACACG    240
ATCTACGCCT TCGCCCGCGA CGGCGTCGGC GCGATCGAGG ACTTCGCGAT CCGCCTCGGT    300
CAGCACTTCG TCGAGGACTT CGAGTGGATC GAGGGCGGCC GCTGGGAGAT CGAGCAGTAC    360
ACCTGGAACC GCATCGAGAC CGCCGACGGC GAGCACGACC ACGCGTTCGT CCGGAACAAC    420
CAGGAGACGC GCACGACGGT CGTCCAGCGC GACGGCGACG AGGTCTTCGT CGTCTCGGGA    480
CTCACGGACC TCGTCGTGCT CAAGTCCACC GGCTCGGAGT TCCACGGGTT CCCGCGCGAC    540
CGCTACACGA CGCTCGTGGA GACCAACGAC CGCATCCTCG CGACGTCGGT CACCTCGCGG    600
TGGCGCTACA CGACCACCGA CGTCGACTTC GACGCCGTGT ACGCGAAGGT CCGCGCGATC    660
CAGCTCGAGG CGTTCGCGAC GACCCACTCC CTCGCGCTCC AGCAGACGCT GTTCGCGATG    720
GGCAAGGCGG TCCTCGAGGC GATCCCGGAG ATCGCCGAGA TCAAGTTCTC GATGCCGAAC    780
AAGCACCACT TCCTCGTGGA CCTCGCGCCG TTCGGCCTCG ACAACCCGAA CGAGGTCTTC    840
TACGCGGCCG ACCGCCCGTA CGGCCTCATC GAGGCGACGG TCCAGCGCGA GGGCGAGCCG    900
GCCGAGCCGC GCGCCTGGGC GACCGTCACC GGGTTCTGCT AATAA                    945
```